(12) United States Patent
Lee et al.

(10) Patent No.: US 10,816,541 B2
(45) Date of Patent: Oct. 27, 2020

(54) METHOD FOR PREDICTING SIDE EFFECT OF WHITENING INGREDIENT

(71) Applicant: AMOREPACIFIC CORPORATION, Seoul (KR)

(72) Inventors: Chang Seok Lee, Yongin-si (KR); Heung Soo Baek, Yongin-si (KR); Yung Hyup Joo, Yongin-si (KR); Jeong Hwan Kim, Yongin-si (KR); Hong-Ju Shin, Yongin-si (KR); Mi Young Park, Yongin-si (KR); Song Seok Shin, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 432 days.

(21) Appl. No.: 15/542,263

(22) PCT Filed: Feb. 26, 2016

(86) PCT No.: PCT/KR2016/001915
§ 371 (c)(1),
(2) Date: Jul. 7, 2017

(87) PCT Pub. No.: WO2016/137270
PCT Pub. Date: Sep. 1, 2016

(65) Prior Publication Data
US 2018/0267022 A1    Sep. 20, 2018

(30) Foreign Application Priority Data

Feb. 27, 2015  (KR) .................. 10-2015-0028474

(51) Int. Cl.
*G01N 33/50* (2006.01)
(52) U.S. Cl.
CPC ..... *G01N 33/5044* (2013.01); *G01N 33/5014* (2013.01)
(58) Field of Classification Search
None
See application file for complete search history.

(56) References Cited

U.S. PATENT DOCUMENTS

| 2006/0104926 A1 | 5/2006 | Nagamine et al. |
| 2013/0177512 A1 | 7/2013 | Kurfurst et al. |

FOREIGN PATENT DOCUMENTS

| CN | 101532950 A | 9/2009 |
| JP | 2004189698 | 7/2004 |
| JP | 2006290749 | 10/2006 |
| JP | 2006526005 | 11/2006 |
| JP | 2012501639 | 1/2012 |
| KR | 1020020073624 A | 9/2002 |
| KR | 1020110018091 A | 2/2011 |
| KR | 101206200 B1 | 11/2012 |

OTHER PUBLICATIONS

Lajis, et al., "Depigmenting Effect of Kojic Acid Esters in Hyperpigmented B16F1 Melanoma Cells, Hindawi Publishing Corporation Journal of Biomedicine and Biotechnology", vol. 2012, Article ID 952452, pp. 1-9.
Heo, et al., "Inhibitory effect of diphlorethohydroxycarmalol on melanogenesis and its protective effect against UV-B radiation-induced cell damage", Food and Chemical Toxicology vol. 48 (2010) pp. 1355-1361.
International Search Report with English Translation for International Application No. PCT/KR2016/001915 dated Jun. 10, 2016.
Park, et al., "Effects of Kojic acid, Arbutin and Vitamin C on cell viability and melanin synthesis in B16BL6 Cells", Journal of the Society of Cosmetic Scientists of Korea, (2003), vol. 29, No. 1, pp. 151-167.

*Primary Examiner* — Heidi Reese
(74) *Attorney, Agent, or Firm* — Cantor Colburn LLP (57) ABSTRACT

In one aspect of the present specification, provided is a method for predicting a side effect of a whitening ingredient, the method comprising measuring at least one of i) the increase in toxicity according to long-term use of a whitening ingredient, ii) the difference between a concentration having whitening effect and a concentration having cell toxicity, and iii) the increase in sensitivity to the whitening ingredient according to ultraviolet pretreatment. In addition, the method has an effect of effectively predicting whether a side effect will occur if the whitening ingredient is used for a long time.

19 Claims, 5 Drawing Sheets

METHOD FOR PREDICTING SIDE EFFECT OF WHITENING INGREDIENT

TECHNICAL FIELD

The present disclosure discloses a method for predicting a side effect of a whitening ingredient.

BACKGROUND ART

There is a great interest in skin whitening cosmetics which brighten your faces. In particular, Oriental women show great interests. There is a good reason why the world's leading cosmetic companies target Oriental women. The Oriental races have a large population and tend to have an unusual attachment for bright skin as compared to white or black races. Not a few women avoid outdoor exercises. Especially, in golf courses, some people play golf wearing masks and covering their arms and legs with clothes.

Whereas sunscreens block UV radiation, skin whitening cosmetics prevent melanin production after UV radiation. The Korea Food & Drug Administration approves functional cosmetics only when the concentration of skin whitening substances is above a predetermined level. It is because the skin whitening substances exhibit their efficacy only when they are present above a predetermined amount. The skin whitening substances prevent melanin production through various mechanisms. For example, they prevent activation of tyrosinase which is an enzyme involved in melanin production, prevent oxidation of tyrosine stimulated by tyrosinase or prevent transfer of melanin from melanocytes to keratinocytes.

However, the skin whitening substances often cause side effects. For instance, Kanebo's skin whitening lines with the functional skin whitening substance 'rhododenol (or rhododendrol)' as main ingredient caused leukoderma-like symptoms in about 16,000 consumers, leading to payment of immense compensations and abrogation of the brand. Kanebo's rhododenol, which was developed as a substance effective in preventing melanin production and sold as a skin whitening cosmetic, its analog raspberry ketone and monobenzone, which depigments the skin of patients with leukoderma, are commonly known to be accompanied by melanin cytotoxicity. In contrast, for rucinol (4-n-butylresorcinol) which exhibits an effect of inhibiting melanin production through a similar mechanism (inhibition of tyrosinase activity), no clinical problem has been reported by consumers of commercialized skin whitening products.

Therefore, the need of screening the safety of the substances through, for example, a system capable of predicting the clinical side effects that may occur after repeated long-term use of the whitening ingredients is increasing. In addition, there is a need of a system for predicting the side effect of whitening ingredients conveniently, quickly and accurately because it is not reasonable to consume long time of several years and immense cost for investigating the safety of the whitening ingredients.

REFERENCE OF RELATED ART (Patent document 1) Korean Patent Registration Publication No. 10-1206200.

DISCLOSURE

Technical Problem

In an aspect, the present disclosure is directed to providing a method for predicting a side effect of a whitening ingredient.

In another aspect, the present disclosure is directed to providing a method for judging a whitening ingredient with remarkably decreased side effect by predicting the side effect of the whitening ingredient.

Technical Solution

In an aspect, the present disclosure provides a method for measuring the increase in cytotoxicity due to long-term use of a whitening ingredient as a method for predicting a side effect of the whitening ingredient.

In another aspect, the present disclosure provides a method for measuring the correlation factor between skin whitening concentration and cytotoxic concentration as a method for predicting a side effect of the whitening ingredient.

In another aspect, the present disclosure provides a method for measuring the increase in sensitivity to the whitening ingredient due to ultraviolet pretreatment as a method for predicting a side effect of the whitening ingredient.

Advantageous Effects

A method for predicting a side effect of a whitening ingredient according to an aspect of the present disclosure provides an effect of effectively predicting the side effect that may occur when the whitening ingredient is used for a long time.

The method for predicting a side effect of a whitening ingredient according to an aspect of the present disclosure provides an effect of conveniently investigating the correlation between skin whitening concentration and cytotoxic concentration.

The method for predicting a side effect of a whitening ingredient according to an aspect of the present disclosure provides an effect of effectively predicting the increase in side effects due to ultraviolet radiation.

BEST MODE

In an aspect, the present disclosure provides a method for predicting a side effect of a whitening ingredient by measuring the increase in toxicity due to long-term use of the whitening ingredient.

In an aspect, the present disclosure provides a method for predicting a side effect of a whitening ingredient, the method including measuring at least one of:

i) increase in toxicity due to long-term use of the whitening ingredient;

ii) difference between skin whitening concentration and cytotoxic concentration; and iii) increase in sensitivity to the whitening ingredient due to ultraviolet pretreatment.

In an aspect, the present disclosure provides a method for predicting a side effect of a whitening ingredient, wherein the increase in toxicity of i) is a ratio of second cytotoxicity measured at 48 hours or longer after treatment of melanocytes with the whitening ingredient to first cytotoxicity measured at 3-36 hours.

In an aspect, the present disclosure provides a method for predicting a side effect of a whitening ingredient, wherein the difference between skin whitening concentration and cytotoxic concentration of ii) is a correlation factor of cytotoxic concentration of the whitening ingredient causing toxicity in melanocytes to effective inhibitory concentration of melanin production of the whitening ingredient effectively inhibiting melanin production by the melanocytes.

In an aspect, the present disclosure provides a method for predicting a side effect of a whitening ingredient, wherein the increase in sensitivity of iii) is a ratio of cytotoxicity of a test group wherein UV-irradiated melanocytes are treated with the whitening ingredient to cytotoxicity of a control group wherein UV-unirradiated melanocytes are treated with the whitening ingredient.

In an aspect, the present disclosure provides a method for predicting a side effect of a whitening ingredient, which includes: a step of adding a whitening ingredient to melanocytes; a step of measuring first cytotoxicity at 3-36 hours after the addition of the whitening ingredient to the melanocytes; a step of measuring second cytotoxicity at 48 hours after the addition of the whitening ingredient to the melanocytes; and a step of measuring a ratio of the second cytotoxicity to the first cytotoxicity.

In an aspect of the present disclosure, the first cytotoxicity may be measured, for example, at 3 hours or later, 4 hours or later, 6 hours or later, 8 hours or later, 10 hours or later, 12 hours or later, 14 hours or later, 16 hours or later, 18 hours or later, 20 hours or later or 22 hours or later.

Also, the first cytotoxicity may be measured, for example, at 36 hours or earlier, 34 hours or earlier, 32 hours or earlier, 30 hours or earlier, 28 hours or earlier, 26 hours or earlier or 24 hours or earlier.

In an aspect of the present disclosure, the second cytotoxicity may be measured, for example, at 48 hours or later, 60 hours or later, 72 hours or later, 84 hours or later, 96 hours or later, 108 hours or later, 120 hours or later, 132 hours or later, 144 hours or later, 156 hours or later, 168 hours or later or 180 hours or later.

Also, the second cytotoxicity may be measured, for example, at 480 hours or earlier, 456 hours or earlier, 432 hours or earlier, 408 hours or earlier, 384 hours or earlier, 360 hours or earlier, 336 hours or earlier, 312 hours or earlier, 288 hours or earlier, 264 hours or earlier, 240 hours or earlier, 216 hours or earlier or 192 hours or earlier.

The ratio of the cytotoxicity may be measured effectively when the measurement is made within the time range described above.

In an aspect of the present disclosure, the cytotoxicity may be cell survivability (%) expressed by the absorbance by cells treated with the whitening ingredient as compared to a control group not treated with the whitening ingredient.

For example, the side effect of the whitening ingredient may be predicted by measuring cell survivability (%) according to Equation 1.

$$\text{Cell survivability (\%)} = \{(A_{sample} - A_b)/(A_c - A_b)\} \times 100 \quad \text{[Equation 1]}$$

$A_{sample}$: absorbance of a sample treated with the whitening ingredient at 450 nm $A_b$: absorbance of a blank $A_c$: absorbance of a vehicle control (0.5% DMSO)

In an aspect of the present disclosure, the cytotoxicity may be $CC_{20}$ (20% cytotoxicity concentration) at which 20% of cells are killed as compared to a control group not treated with the whitening ingredient. The $CC_{20}$ is usually regarded as the concentration at which cytotoxicity begins to appear.

In an aspect of the present disclosure, the cytotoxicity may be $CC_{50}$ (50% cytotoxicity concentration) at which half of cells are killed as compared to a control group not treated with the whitening ingredient. The $CC_{50}$ is the concentration at which half of cells are killed as compared to the vehicle control group.

In an aspect of the present disclosure, the ratio of the second cytotoxicity to the first cytotoxicity may be measured as a fold value.

In another aspect, the present disclosure provides a method for predicting a side effect of a whitening ingredient, which includes measuring difference between skin whitening concentration and cytotoxic concentration. For example, the difference between skin whitening concentration and cytotoxic concentration may be measured by measuring cytotoxic concentration after treating melanocytes with the whitening ingredient, measuring effective inhibitory concentration of melanin production of the melanocytes after the treatment and measuring a correlation factor of the cytotoxic concentration as compared to the effective inhibitory concentration of melanin production.

In another aspect, the present disclosure provides a method for predicting a side effect of a whitening ingredient, which includes: a step of measuring cytotoxic concentration at 3-480 hours after adding the whitening ingredient to melanocytes; a step of measuring $EC_{50}$, or the effective concentration of inhibiting melanin production by 50%, at 3-480 hours after adding the whitening ingredient to melanocytes; and a step of measuring a correlation factor of the cytotoxic concentration and the effective inhibitory concentration of melanin production ($EC_{50}$) by dividing the cytotoxicity by $EC_{50}$.

In another aspect, the present disclosure provides a method for predicting a side effect of a whitening ingredient, wherein the cytotoxic concentration is $CC_{50}$ (50% cytotoxicity concentration) at which half of cells are killed as compared to a control group or $CC_{20}$ (20% cytotoxicity concentration) at which 20% of cells are killed as compared to a control group.

In another aspect of the present disclosure, the cytotoxicity may be measured, for example, at 3 hours or later, 6 hours or later, 12 hours or later, 24 hours or later, 48 hours or later, 60 hours or later, 72 hours or later, 84 hours or later, 96 hours or later, 108 hours or later, 120 hours or later, 132 hours or later, 144 hours or later, 156 hours or later, 168 hours or later or 180 hours or later.

Also, the cytotoxicity may be measured, for example, at 480 hours or earlier, 456 hours or earlier, 432 hours or earlier, 408 hours or earlier, 384 hours or earlier, 360 hours or earlier, 336 hours or earlier, 312 hours or earlier, 288 hours or earlier, 264 hours or earlier, 240 hours or earlier, 216 hours or earlier or 192 hours or earlier.

In another aspect of the present disclosure, the effective concentration $EC_{50}$ may be measured, for example, at 3 hours or later, 6 hours or later, 12 hours or later, 24 hours or later, 48 hours or later, 60 hours or later, 72 hours or later, 84 hours or later, 96 hours or later, 108 hours or later, 120 hours or later, 132 hours or later, 144 hours or later, 156 hours or later, 168 hours or later or 180 hours or later.

Also, the effective concentration $EC_{50}$ may be measured, for example, at 480 hours or earlier, 456 hours or earlier, 432 hours or earlier, 408 hours or earlier, 384 hours or earlier, 360 hours or earlier, 336 hours or earlier, 312 hours or earlier, 288 hours or earlier, 264 hours or earlier, 240 hours or earlier, 216 hours or earlier or 192 hours or earlier.

The correlation factor between the skin whitening effect (the effective inhibitory concentration of melanin production by melanocytes) and the cytotoxic concentration may be measured effectively when the measurement is made within the time range described above.

In another aspect, the present disclosure provides a method for predicting a side effect of a whitening ingredient by measuring the increase in sensitivity to the whitening ingredient due to ultraviolet pretreatment.

For example, the increase in sensitivity may be measured by measuring the cytotoxicity of a test group wherein UV-irradiated melanocytes are treated with the whitening ingredient, measuring the cytotoxicity of a control group wherein UV-unirradiated melanocytes are treated with the whitening ingredient and measuring the ratio of the cytotoxicity of the test group and the control group.

In another aspect, the present disclosure provides a method for predicting a side effect of a whitening ingredient, which includes: a step of measuring the cytotoxicity of the test group at 3-480 hours after treating UV-irradiated melanocytes with the whitening ingredient and measuring the cytotoxicity of the control group at 3-480 hours after treating UV-unirradiated melanocytes with the whitening ingredient; and a step of measuring the ratio of the cytotoxicity of the test group and the control group.

In another aspect, the present disclosure provides a method for predicting a side effect of a whitening ingredient, wherein the cytotoxicity of the test group and the control group is the cell survivability (%) according to Equation 1.

In another aspect of the present disclosure, the cytotoxicity of the test group and the control group may be measured, for example, at 3 hours or later, 6 hours or later, 12 hours or later, 24 hours or later, 48 hours or later, 60 hours or later, 72 hours or later, 84 hours or later, 96 hours or later, 108 hours or later, 120 hours or later, 132 hours or later, 144 hours or later, 156 hours or later, 168 hours or later or 180 hours or later.

Also, the cytotoxicity of the test group and the control group may be measured, for example, at 480 hours or earlier, 456 hours or earlier, 432 hours or earlier, 408 hours or earlier, 384 hours or earlier, 360 hours or earlier, 336 hours or earlier, 312 hours or earlier, 288 hours or earlier, 264 hours or earlier, 240 hours or earlier, 216 hours or earlier or 192 hours or earlier.

The increase in sensitivity to the whitening ingredient due to ultraviolet pretreatment may be measured effectively when the measurement is made within the time range described above.

In another aspect of the present disclosure, the intensity of the UV may be 0.1 $mJ/cm^3$ or higher, 0.5 $mJ/cm^3$ or higher, 1 $mJ/cm^3$ or higher, 2 $mJ/cm^3$ or higher, 3 $mJ/cm^3$ or higher, 4 $mJ/cm^3$ or higher, 5 $mJ/cm^3$ or higher, 6 $mJ/cm^3$ or higher, 7 $mJ/cm^3$ or higher, 8 $mJ/cm^3$ or higher, 9 $mJ/cm^3$ or higher, 10 $mJ/cm^3$ or higher, 11 $mJ/cm^3$ or higher, 12 $mJ/cm^3$ or higher, 13 $mJ/cm^3$ or higher, 14 $mJ/cm^3$ or higher, 15 $mJ/cm^3$ or higher, 16 $mJ/cm^3$ or higher, 17 $mJ/cm^3$ or higher, 18 $mJ/cm^3$ or higher, 19 $mJ/cm^3$ or higher or 20 $mJ/cm^3$ or higher.

Also, the intensity of the UV may be 500 $mJ/cm^3$ or lower, 480 $mJ/cm^3$ or lower, 460 $mJ/cm^3$ or lower, 44 $mJ/cm^3$ or lower, 420 $mJ/cm^3$ or lower, 400 $mJ/cm^3$ or lower, 380 $mJ/cm^3$ or lower, 360 $mJ/cm^3$ or lower, 340 $mJ/cm^3$ or lower, 320 $mJ/cm^3$ or lower, 300 $mJ/cm^3$ or lower, 280 $mJ/cm^3$ or lower, 260 $mJ/cm^3$ or lower, 240 $mJ/cm^3$ or lower, 220 $mJ/cm^3$ or lower, 200 $mJ/cm^3$ or lower, 180 $mJ/cm^3$ or lower, 160 $mJ/cm^3$ or lower, 140 $mJ/cm^3$ or lower, 120 $mJ/cm^3$ or lower, 100 $mJ/cm^3$ or lower, 80 $mJ/cm^3$ or lower, 60 $mJ/cm^3$ or lower or 40 $mJ/cm^3$ or lower.

The increase in sensitivity to the whitening ingredient due to ultraviolet pretreatment may be measured effectively when the measurement is made within the time range described above.

In another aspect, the present disclosure provides a method for predicting a side effect of a whitening ingredient, which includes measuring one of those described above.

The side effect of a whitening ingredient is various and representative side effects include skin aging, carcinogenesis, acne, chapping, leukoderma, etc. The most typical side effect of them is leukoderma. The whitening ingredients known to cause leukoderma-like side effects include rhododenol, raspberry ketone and monobenzone. In the present disclosure, these whitening ingredients are used as positive compounds for melanin cytotoxicity. In 1998, Dr. Okubo of POLA Chemical Industries developed 4-butylresorcinol isolated from fir as a substance having skin whitening effect. It was released in the market in 1999 with the name rucinol. This whitening ingredient has been used in skin whitening products for over 15 years. Because no clinical side effect has been reported by the users of those products, rucinol whose safety has been proven through long-term use is used in the present disclosure as a negative compound for melanin cytotoxicity.

MODE FOR INVENTION

Hereinafter, the present disclosure will be described in detail through examples. However, the following examples are for illustrative purposes only and the scope of the present disclosure is not limited by the examples.

Preparation of Whitening Ingredients (Test Substances)

Figure 1:
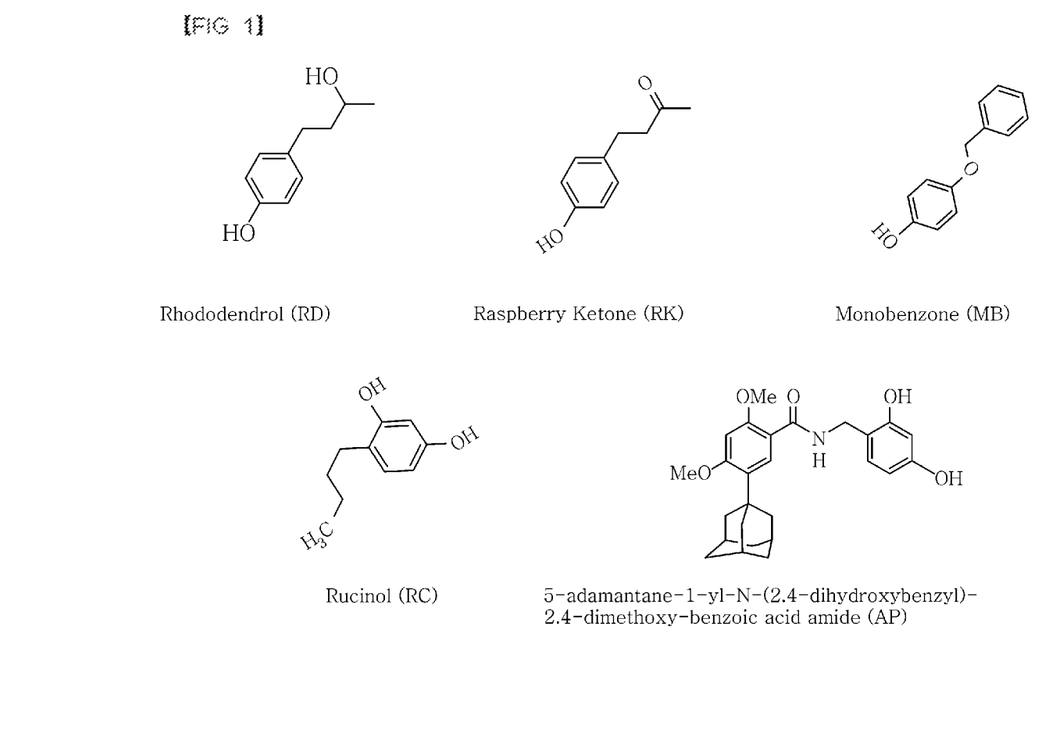
FIG. 1 shows the structure of the test substances used in test examples as whitening ingredients.

Test substances were rhododenol (>98%), raspberry ketone (>98%), monobenzone (>98%), rucinol (>98%) and 5-adamantan-1-yl-N-(2,4-dihydroxybenzyl)-2,4-dimethoxy-benzoic acid amide (>98%). The rhododenol, the raspberry ketone and the 5-adamantan-1-yl-N-(2,4-dihydroxybenzyl)-2,4-dimethoxy-benzoic acid amide were synthesized (FIG. 1). In particular, the 5-adamantan-1-yl-N-(2, 4-dihydroxybenzyl)-2,4-dimethoxy-benzoic acid amide (hereinafter 'AP'), which is a substance synthesized by the inventors of the present disclosure, has the structure of Chemical Formula 1 and was found to exhibit excellent inhibitory effect of melanin production by melanocytes in Test Example 2.

5-Adamantan-1-yl-N-(2,4-dihydroxybenzyl)-2,4-dimethoxy-benzoic acid amide

[Chemical Formula 1]

The monobenzone (4-benzyloxy-phenol) was purchased from Santa Cruz Biotechnology (USA, Cat. No. sc-232257) and the rucinol (4-butylresorcinol) was purchased from Tokyo Chemical Industry (Japan, Cat. No. B3773). All the test substances were dissolved in DMSO and were treated to cells with a final concentration of 0.5% in DMSO.

Preparation of Melanocytes

HEMn-MP and A375 cells were used for experiments.

The HEMn-MP (human epidermal melanocytes, neonatal, moderately pigmented donor, Cat. No. C-102-5C) cells were purchased from Life Technologies (USA). As a cell culture medium, medium 254 (Cat. No. M-254-500) supplemented with HMGS (Cat. No. S-002-5) was used. The cells were cultured according to the manufacturer's manual and cells during passages 3-8 were used. To summarize, the cells were cultured on a 175 T flask in a 5% $CO_2$ incubator at 37° C. During subculturing, the cells were separated using 0.05% trypsin-EDTA, collected by centrifugation (1200 rpm, 5 minutes) and cultured after seeding to $5 \times 10^3$ cells/cm$^2$. For cytotoxicity test, the cells were seeded onto a 96-well plate with $2 \times 10^4$ cells/well, cultured for a day and treated with each substance at 200 μL/well. Then, cytotoxicity was measured after a predetermined time.

The A375 (human melanoma cell line) cells were purchased from the ATCC (Cat. No. CRL-1619, USA). As a cell culture medium, DMEM (Cat. No. 12-604, Lonza, USA) supplemented with 10% FBS (Cat. No. 16000-044, Gibco, USA) was used. Subculturing and cytotoxicity test were conducted in the same manner as for the HEM cells.

Measurement of Cytotoxicity

Cytotoxicity was measured with Cell Counting Kit-8 (CCK-8) manufactured by Dojindo Molecular Technologies (USA). After removing the medium from the 96-well plate, 200 μL of 10% CCK-8 in the same medium was added to each well. After incubation at 37° C. for about 2 hours, absorbance of 100 μL of the medium was measured at 450 nm using an ELISA reader. As the cells are killed, the color of CCK-8 shifts to longer wavelength from colorless to orange color.

Cell survivability was calculated according to Equation 1.

Cell survivability (%)=$\{(A_{sample}-A_b)/(A_c-A_b)\} \times 100$  [Equation 1]

$A_{sample}$: absorbance of a sample treated with the whitening ingredient at 450 nm $A_b$: absorbance of a blank $A_c$: absorbance of a vehicle control (0.5% DMSO)

Statistical Analysis

The data were statistically analyzed by the Student's t-test. Mean and standard deviation (SD) were obtained based on the result of three or more independent tests.

Figure 2:
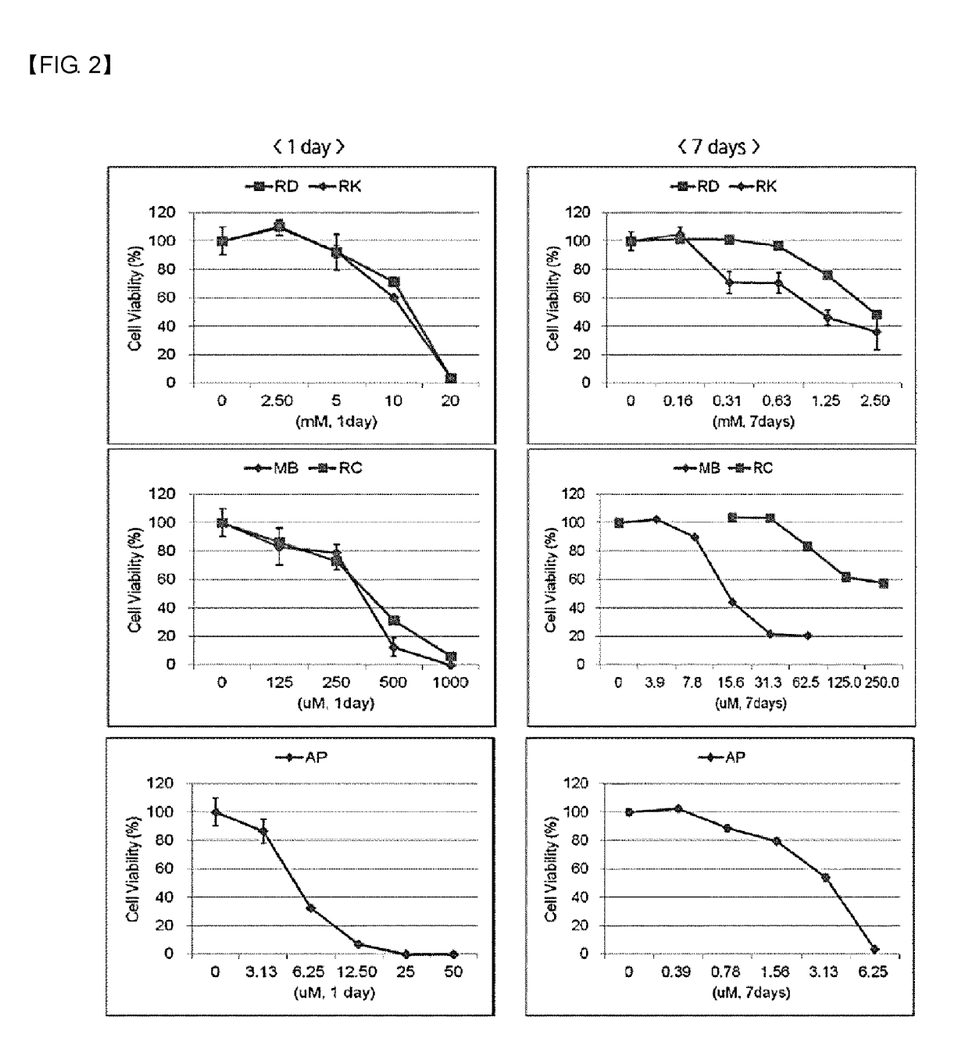
FIG. 2 shows the cytotoxicity for samples on days 1 and 7 at different concentrations measured in Test Example 1-1. RD represents rhododenol, RK represents raspberry ketone, MB represents monobenzone, RC represents rucinol and AP represents 5-adamantan-1-yl-N-(2,4-dihydroxybenzyl)-2,4-dimethoxy-benzoic acid amide.

Test Example 1-1: Comparison of Cytotoxic Concentration for HEMn-MP Cells Depending on Whitening Ingredients and Treatment Time In order to determine the cytotoxic concentration of the whitening ingredients for HEMn-MP (human epidermal melanocytes, neonatal, moderately pigmented donor, Cat. No. C-102-5C) cells, cell survivability (% cell survival rate) was measured as compared to a control group (0.5% DMSO) on days 1 and 7 after treatment with each whitening ingredient at the concentration described in Table 1 (FIG. 2). Based on the measurement result, $CC_{20}$ and $CC_{50}$ were calculated for the whitening ingredients and treatment time. Then, the ratio of the cytotoxic concentration on day 7 as compared to day 1 was calculated (Table 2).

TABLE 1

|  | Concentration (day 1) | Concentration (day 7) |
|---|---|---|
| RD (rhododenol)/RK (raspberry ketone) | 2.5 mM | 0.16 mM |
|  | 5 mM | 0.31 mM |
|  | 10 mM | 0.63 mM |
|  | 20 mM | 1.25 mM |
|  |  | 2.50 mM |
| MB (monobenzone)/RC (rucinol) | 125 μM | 3.9 μM |
|  | 250 μM | 7.8 μM |
|  | 500 μM | 15.6 μM |
|  | 1000 μM | 31.3 μM |
|  |  | 62.5 μM |
|  |  | 125.0 μM |
|  |  | 250.0 μM |
| AP (5-adamantan-1-yl-N-(2,4-dihydroxybenzyl)-2,4-dimethoxy-benzoic acid amide) | 3.13 μM | 0.39 μM |
|  | 6.25 μM | 0.78 μM |
|  | 12.50 μM | 1.56 μM |
|  | 25 μM | 3.13 μM |
|  | 50 μM | 6.25 μM |

TABLE 2

| Whitening ingredients |  | RD (mM) | RK (mM) | MB (μM) | RC (μM) | AP (μM) |
|---|---|---|---|---|---|---|
| Day 1 | $CC_{20}$ | 7.1 ± 0.8 | 6.5 ± 0.2 | 178.2 ± 21.6 | 170.2 ± 15.9 | 3.3 ± 0.4 |
|  | $CC_{50}$ | 10.8 ± 0.7 | 10.4 ± 0.2 | 284.3 ± 28.2 | 346.7 ± 12.7 | 5.4 ± 0.3 |
| Day 7 | $CC_{20}$ | 1.0 ± 0.0 | 0.4 ± 0.1 | 8.9 ± 0.4 | 69.7 ± 6.1 | 1.3 ± 0.0 |
| Ratio of on day 7 as | $CC_{50}$ | 2.4 ± 0.1 | 1.4 ± 0.4 | 19.0 ± 0.7 | 283.8 ± 20.4 | 2.5 ± 0.0 |
| compared to day 1 | $CC_{20}$ | 7.1 | 16.3 | 20 | 2.4 | 2.5 |
| (fold) | $CC_{50}$ | 4.5 | 7.4 | 14.9 | 1.2 | 2.2 |

In the toxicity test using the HEMn-MP cells, the cytotoxicity for the whitening ingredients varied significantly depending on the exposure time. Among the whitening ingredients, RD, RK and MB which are known to have side effects showed 4.5-14.9 fold increased cytotoxicity ($CC_{50}$) on day 7 as compared to day 1. In contrast, RC (1.2 fold) and AP (2.2 fold) which have no clinically reported side effect yet showed relatively less increase in cytotoxicity (Table 2). This reveals that the increase in toxicity varies depending on the treatment (exposure) time of the sample. Interestingly, this phenomenon was particularly distinct for RD, RK and MB which are known to cause leukoderma (melanocytotoxicity). To conclude, it can be determined that there is a side effect of a whitening ingredient when the cytotoxicity on day 7 is 2.7 fold or higher, 2.8 fold or higher, 2.9 fold or higher, 3.0 fold or higher, 3.1 fold or higher, 3.2 fold or higher, 3.3 fold or higher, 3.4 fold or higher, 3.5 fold or higher, 3.6 fold or higher, 3.7 fold or higher, 3.8 fold or higher, 3.9 fold or higher, 4.0 fold or higher, 4.1 fold or higher, 4.2 fold or higher, 4.3 fold or higher or 4.4 fold or higher as compared to the cytotoxicity on day 1.

Figure 3:
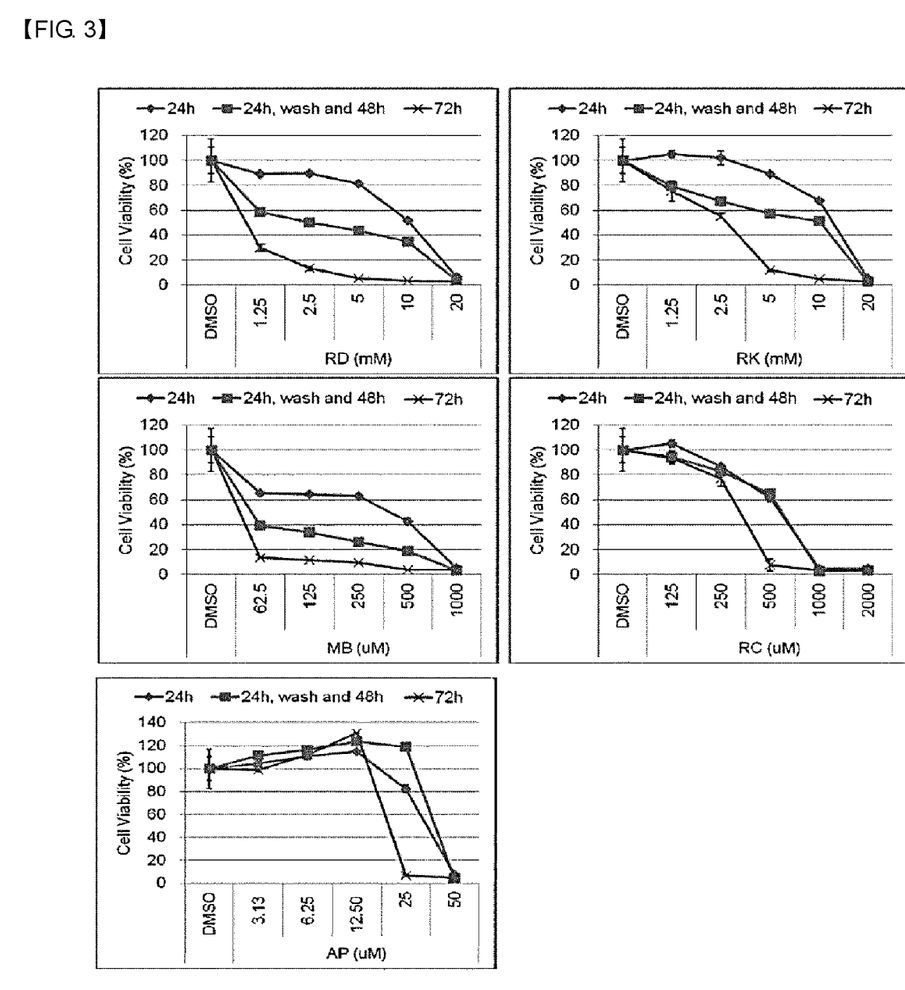
FIG. 3 shows the cytotoxicity measured in Test Example 1-2 after treating with samples for 24 hours, the cytotoxicity measured after treating with samples for 24 hours and 48 hours later after exchanging with fresh media, and the cytotoxicity measured after treating with samples for 72 hours.

Test Example 1-2: Comparison of Cytotoxic Concentration for A375 Cells Depending on Whitening Ingredients and Treatment Time The cytotoxicity of the whitening ingredients for A375 (human melanoma cell line, Cat. No. CRL-1619) cells with different treatment time was investigated. The toxicity was measured for 3 different sample treatment conditions. The cytotoxicity was measured after treating with the whitening ingredients for 24 hours, after treating with the samples for 24 hours and 48 hours later after exchanging with fresh media, and after treating with the samples for 72 hours without exchange of media. The result is shown as graphs (FIG. 3). Based on the measurement result, $CC_{20}$ and $CC_{50}$ were calculated for the whitening ingredients and treatment time. Then, the ratio of the cytotoxic concentration on day 3 as compared to day 1 was calculated (Table 3).

TABLE 3

| Whitening ingredients | | RD (mM) | RK (mM) | MB (μM) | RC (μM) | AP (μM) |
|---|---|---|---|---|---|---|
| Day 1 | $CC_{20}$ | 4.2 ± 0.2 | 6.7 ± 0.1 | 119.8 ± 4.7 | 313.9 ± 10.6 | 25.5 ± 0.8 |
|  | $CC_{50}$ | 8.4 ± 0.2 | 10.7 ± 0.1 | 294.8 ± 7.2 | 508.4 ± 11.3 | 33.8 ± 0.7 |
| Day 3 | $CC_{20}$ | 0.19 ± 0.01 | 0.24 ± 0.02 | 2.31 ± 0.07 | 52.73 ± 4.67 | 17.2 ± 0.09 |
|  | $CC_{50}$ | 0.50 ± 0.02 | 0.79 ± 0.04 | 7.19 ± 0.14 | 122.13 ± 10.99 | 19.99 ± 0.06 |
| Ratio of on day 3 as | $CC_{20}$ | 22.1 | 27.9 | 51.8 | 6.0 | 1.5 |
| Compared to day 1 (fold) | $CC_{50}$ | 16.8 | 13.5 | 41 | 4.2 | 1.7 |

Also for the A375 cells, the cytotoxicity on day 3 after treatment with RD, RK and MB was increased by about 16.8-41 fold ($CC_{50}$) as compared to day 1, whereas the increase in toxicity was less for RC (4.2 fold) and AP (1.7 fold) (Table 3). RD, RK and MB showed significant increase in toxicity with time, suggesting that the toxicity for melanocytes treated with these samples is proportional to time. This is regarded as one of the characteristics of in-vitro melanocytotoxicity of leukoderma-causing samples. To conclude, it can be determined that there is a side effect of a whitening ingredient when the cytotoxicity on day 3 is 7 fold or higher, 7.5 fold or higher, 8 fold or higher, 8.5 fold or higher, 9 fold or higher, 9.5 fold or higher, 10 fold or higher, 10.5 fold or higher, 11 fold or higher, 11.5 fold or higher or 12 fold or higher as compared to the cytotoxicity on day 1. In particular, when the A375 cells were treated with the samples for a day and then cultured further for 2 days after removing the samples, the groups treated with the RD, RK and MB samples showed continuously increased toxicity whereas the groups treated with RC and AP showed no more increase in cytotoxicity. This suggests that the recovery of cytotoxicity after removal of the samples is different depending on the samples. This is another difference between the whitening ingredients causing leukoderma and the RC and AP whitening ingredients (FIG. 2).

Figure 4:
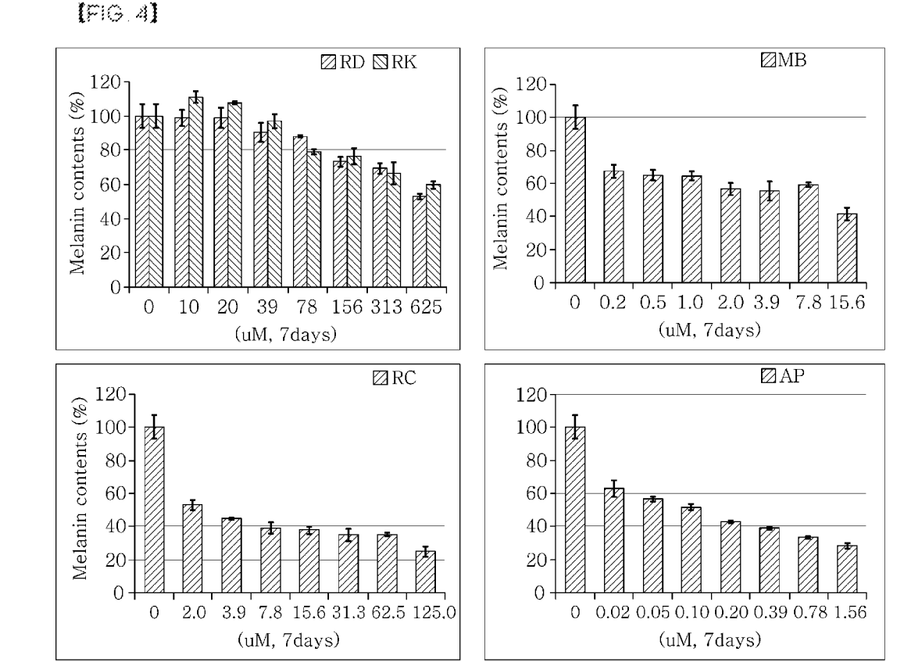
FIG. 4 compares the inhibitory concentration of melanin synthesis for samples on day 7 measured in Test Example 2.

Test Example 2: Comparison of Correlation of Cytotoxic Concentration and Effective Concentration of Whitening Ingredients for HEMn-MP Cells The inhibitory effect of melanin production of the whitening ingredients for HEMn-MP cells was investigated. After treating the cells with the samples at concentrations shown in Table 4 and culturing for 7 days, the amount of melanin was measured as compared to a control group (0.5% DMSO) (FIG. 4). Also, $EC_{50}$ (50% effective inhibitory concentration of melanin production) was calculated for the whitening ingredients (Table 5). Then, $CC_{20}$ or $CC_{50}$ was divided by $EC_{50}$ to investigate the correlation factor (difference) between the cytotoxicity and the effective inhibitory concentration of melanin production (Table 6).

TABLE 4

|  | Concentration (day 7) |
|---|---|
| RD and RK | 10 μM |
|  | 20 μM |
|  | 39 μM |
|  | 78 μM |
|  | 156 μM |
|  | 313 μM |
|  | 625 μM |
| MB | 0.2 μM |
|  | 0.5 μM |
|  | 1.0 μM |

TABLE 4-continued

|  | Concentration (day 7) |
|---|---|
|  | 2.0 μM |
|  | 3.9 μM |
|  | 7.8 μM |
|  | 15.6 μM |
| RC | 2.0 μM |
|  | 3.9 μM |
|  | 7.8 μM |
|  | 15.6 μM |
|  | 31.3 μM |
|  | 62.5 μM |
|  | 125.0 μM |
| AP | 0.02 μM |
|  | 0.05 μM |
|  | 0.10 μM |

TABLE 4-continued

| Concentration (day 7) |
|---|
| 0.20 µM |
| 0.39 µM |
| 0.78 µM |
| 1.56 µM |

TABLE 5

| | Concentration | | | | |
|---|---|---|---|---|---|
| | RD (mM) | RK (mM) | MB (µM) | RC (µM) | AP (µM) |
| $EC_{50}$ | 1.13 ± 0.16 | 0.97 ± 0.09 | 6.8 ± 2.5 | 2.7 ± 0.6 | 0.11 ± 0.01 |

*$EC_{50}$ (50% inhibitory concentration of melanin synthesis)

TABLE 6

| Fold | RD | RK | MB | RC | AP |
|---|---|---|---|---|---|
| $CC_{20}/EC_{50}$ | 0.8 | 0.4 | 1.3 | >20 | 11.8 |
| $CC_{50}/EC_{50}$ | 2.1 | 1.4 | 2.8 | >20 | >20 |

Table 6 compares the correlation factor between the cytotoxic concentration ($CC_{50}$) and the inhibitory concentration of melanin synthesis ($EC_{50}$) of the whitening ingredients on day 7. $CC_{20}/EC_{50}$ is the value obtained by dividing the 20% cytotoxic concentration by the 50% effective inhibitory concentration of melanin production and represents the correlation factor of the 20% cytotoxic concentration and the effective concentration. $CC_{50}/EC_{50}$ is the value obtained by dividing the 50% cytotoxic concentration by the 50% effective inhibitory concentration of melanin production and represents the correlation factor of the 50% cytotoxic concentration and the effective concentration.

Whereas RD, RK and MB showed 50% cytotoxicity at 1.4-2.8 fold, RC and AP showed 50% cytotoxicity only at 20 fold or higher (Table 6). That is to say, whereas RD, RK and MB showed a very narrow difference between the effective concentration and the cytotoxic concentration, i.e., the in-vitro safety margin, RC and AP showed a broad safety margin. Accordingly, it can be determined that the whitening ingredient is safe when the $CC_{50}/EC_{50}$ is 5 fold or higher, 6 fold or higher, 7 fold or higher, 8 fold or higher, 9 fold or higher, 10 fold or higher, 11 fold or higher, 12 fold or higher, 13 fold or higher, 14 fold or higher, 15 fold or higher, 16 fold or higher, 17 fold or higher, 18 fold or higher, 19 fold or higher or 20 fold or higher.

This phenomenon suggests that the inhibitory effect of melanin production may cause death of melanocytes for some samples. This is an important factor in that safety should be ensured in the development of cosmetics.

Figure 5:
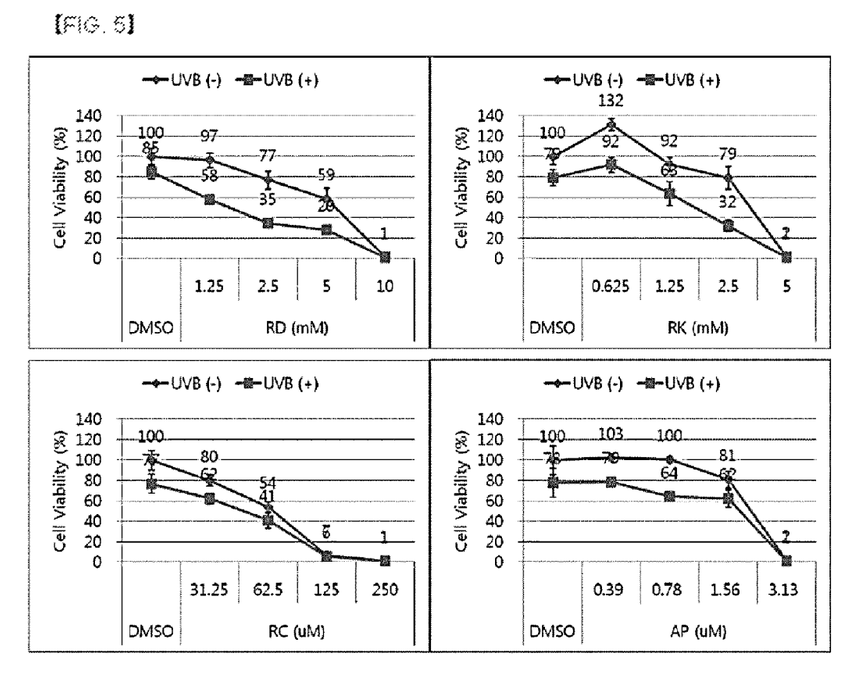
FIG. 5 compares the change in cytotoxicity with or without UVB radiation for 7 days measured in Test Example 3.

Test Example 3: Comparison of Toxic Concentration (Increase in Sensitivity to Whitening Ingredients) of Whitening Ingredients for HEMn-MP Cells Depending on UVB Radiation In order to investigate the effect of UVB radiation on the cytotoxicity of the whitening ingredients, cytotoxicity was compared for groups treated with the whitening ingredients without UVB radiation and groups irradiated with UVB at 20 mJ/cm³ and then treated with the whitening ingredients (FIG. 5). That is to say, the response of the cells excited by UVB radiation to various whitening ingredients was investigated. After irradiating the cells with UVB and treating the cells with the samples, increase in cytotoxicity was determined and the ratio of cytotoxicity as compared to before the treatment was calculated (Table 7).

TABLE 7

| RD | Concentration (mM) | 1.25 | 2.5 | 5 | Mean |
|---|---|---|---|---|---|
| | Ratio of cytotoxicity | 24% | 27% | 15% | 22% |
| RK | Concentration (mM) | 0.625 | 1.25 | 2.5 | Mean |
| | Ratio of cytotoxicity | 19% | 8% | 26% | 18% |
| RC | Concentration (µM) | 31.25 | 62.5 | 125 | Mean |
| | Ratio of cytotoxicity | 0% | 0% | 0% | 0% |
| AP | Concentration (µM) | 0.39 | 0.78 | 1.56 | Mean |
| | Ratio of cytotoxicity | 2% | 14% | 0% | 5% |

Table 7 shows the change in cytotoxicity on day 7 for the whitening ingredients with or without UVB radiation. The ratio (%) of toxicity for the UVB-irradiated cells as compared to UVB-unirradiated cells was determined at representative concentrations (3 points) for each whitening ingredient. The ratio was corrected for the cytotoxicity of the control group (15-20%).

When the melanocytes were irradiated with UVB and then treated with the whitening ingredients, RD and RK showed about 20% increased cytotoxicity on average, whereas RC and AP showed insignificant increase in cytotoxicity of less than 5%. This means that the melanocytes excited by UVB radiation show aggravated toxicity when treated with RD and RK. This phenomenon is not observed for RC and AP and is regarded as one of the characteristics of the whitening ingredients causing leukoderma with a narrow safety margin. To conclude, it can be determined that the whitening ingredient is safe when the ratio is 15% or lower, 14% or lower, 13% or lower, 12% or lower, 11% or lower, 10% or lower, 9% or lower, 8% or lower or 7% or lower on average.

To summarize, it can be seen that RD, RK and MB aggravate cytotoxicity when they are treated on melanocytes for longer time and when the cells are exposed to UVB. This is consistent with the fact that leukoderma side effects were reported by the users of rhododenol-containing cosmetics who used them for a long period of time, especially on parts exposed to UV.

Accordingly, in accordance with the method for predicting a side effect of a whitening ingredient according to an aspect of the present disclosure, the side effect of a whitening ingredient due to long-term use can be predicted, the correlation between the skin whitening concentration and the cytotoxic concentration can be elucidated conveniently and the increase in side effects due to UV radiation can be predicted effectively.

The invention claimed is:

1. A method for predicting whether a skin whitening ingredient will cause side effects, the method comprising measuring at least one of:
   i) increase in toxicity due to long-term use of the skin whitening ingredient;
   ii) difference between skin whitening effect concentration and cytotoxic concentration; and
   iii) increase in sensitivity to the skin whitening ingredient due to ultraviolet pretreatment,
   wherein the skin whitening effect concentration is the skin whitening ingredient concentration effective to inhibit a selected amount of melanin production by melanocytes compared to control melanocytes not treated with the skin whitening ingredient, and the cytotoxic concentration is a concentration of the skin whitening ingredient causing a selected level of cell death in a population of melanocytes relative to a control population of melanocytes not treated with the skin whitening ingredient.

2. The method according to claim 1, wherein the increase in toxicity of i) is a ratio of second cytotoxic concentration measured at 48 hours or longer after treatment of melanocytes with the skin whitening ingredient to first cytotoxic concentration measured at 3-36 hours after treatment of melanocytes with the skin whitening ingredient.

3. The method according to claim 1, wherein the difference between skin whitening effect concentration and cytotoxic concentration of ii) is a correlation factor of the cytotoxic concentration to concentration.

4. The method according to claim 1, wherein the increase in sensitivity of iii) is a ratio of cytotoxic concentration of a test group wherein UV-irradiated melanocytes are treated with the skin whitening ingredient to cytotoxic concentration of a control group wherein UV-unirradiated melanocytes are treated with the skin whitening ingredient.

5. The method according to claim 1, wherein the measurement comprises measurement of cell survivability (%) expressed by the absorbance by cells treated with the skin whitening ingredient as compared to a control group not treated with the skin whitening ingredient.

6. The method according to claim 1, wherein the measurement comprises measurement of $CC_{20}$ (20% cytotoxicity concentration) at which 20% of cells are killed as compared to a control group not treated with the skin whitening ingredient.

7. The method according to claim 1, wherein the measurement comprises measurement of $CC_{50}$ (50% cytotoxicity concentration) at which half of cells are killed as compared to a control group not treated with the skin whitening ingredient.

8. The method according to claim 3, wherein the skin whitening effect concentration is the skin whitening ingredient concentration effective to inhibit 50% ($EC_{50}$) of melanin production by melanocytes compared to control melanocytes not treated with the skin whitening ingredient.

9. The method according to claim 4, wherein the melanocytes are irradiated with UV with an intensity of 0.1-500 mJ/cm$^3$.

10. The method according to claim 2, which further comprises determining that the skin whitening ingredient will cause side effects when the ratio of the second cytotoxic concentration to the first cytotoxic concentration of i) is 3 or greater.

11. The method according to claim 3, which further comprises determining that the skin whitening ingredient is safe when the correlation factor of ii) is 10 or greater.

12. The method according to claim 4, which further comprises determining that the skin whitening ingredient is safe when the ratio of iii) is lower than 15% on average.

13. The method according to claim 2, wherein the measurement comprises measurement of cell survivability (%) expressed by the absorbance by cells treated with the skin whitening ingredient as compared to a control group not treated with the skin whitening ingredient.

14. The method according to claim 3, wherein the measurement comprises measurement of cell survivability (%) expressed by the absorbance by cells treated with the skin whitening ingredient as compared to a control group not treated with the skin whitening ingredient.

15. The method according to claim 4, wherein the measurement comprises measurement of cell survivability (%) expressed by the absorbance by cells treated with the skin whitening ingredient as compared to a control group not treated with the skin whitening ingredient.

16. The method according to claim 2, wherein the measurement comprises measurement of $CC_{20}$ (20% cytotoxicity concentration) at which 20% of cells are killed as compared to a control group not treated with the skin whitening ingredient.

17. The method according to claim 3, wherein the measurement comprises measurement of $CC_{20}$ (20% cytotoxicity concentration) at which 20% of cells are killed as compared to a control group not treated with the skin whitening ingredient.

18. The method according to claim 2, wherein the measurement comprises measurement of $CC_{50}$ (50% cytotoxicity concentration) at which half of cells are killed as compared to a control group not treated with the skin whitening ingredient.

19. The method according to claim 3, wherein the measurement comprises measurement of $CC_{50}$ (50% cytotoxicity concentration) at which half of cells are killed as compared to a control group not treated with the skin whitening ingredient.

* * * * *